(12) United States Patent
Arcusa Villacampa

(10) Patent No.: US 10,780,292 B2
(45) Date of Patent: Sep. 22, 2020

(54) HANDPIECE FOR LASER DEVICE

(71) Applicant: INTERMÈDIC ARFRAN, S.A., Barcelona (ES)

(72) Inventor: Francisco Javier Arcusa Villacampa, Barcelona (ES)

(73) Assignee: INTERMÈDIC ARFRAN, S.A., Barcelona (ES)

( * ) Notice: Subject to any disclaimer, the term of this patent is extended or adjusted under 35 U.S.C. 154(b) by 61 days.

(21) Appl. No.: 15/995,715

(22) Filed: Jun. 1, 2018

(65) Prior Publication Data

US 2018/0280087 A1      Oct. 4, 2018

Related U.S. Application Data

(63) Continuation of application No. PCT/ES2016/070856, filed on Dec. 1, 2016.

(30) Foreign Application Priority Data

Dec. 3, 2015 (ES) .................................. 201531355

(51) Int. Cl.
*A61B 18/20* (2006.01)
*A61N 5/06* (2006.01)
(Continued)

(52) U.S. Cl.
CPC .......... *A61N 5/0616* (2013.01); *A61B 18/201* (2013.01); *A61N 5/0603* (2013.01);
(Continued)

(58) Field of Classification Search
None
See application file for complete search history.

(56) References Cited

U.S. PATENT DOCUMENTS

| | | | |
|---|---|---|---|
| 8,709,057 B2 * | 4/2014 | Tettamanti | A61N 5/0603 606/9 |
| 10,080,908 B2 * | 9/2018 | Kazic | A61N 5/0603 |
| 2016/0242847 A1 * | 8/2016 | Yoon | A61B 18/20 |

FOREIGN PATENT DOCUMENTS

| | | |
|---|---|---|
| CN | 104645505 A | 5/2015 |
| ES | 2440795 T3 | 1/2014 |
| | (Continued) | |

OTHER PUBLICATIONS

Baharlou, Simin; International Preliminary Report on Patentability with English Translation of Written Opinion of the International Searching Authority for International Application No. PCT/ES2016/070856; dated Jun. 5, 2018.

(Continued)

*Primary Examiner* — Brian T Gedeon
(74) *Attorney, Agent, or Firm* — Thomas E. Lees, LLC

(57) ABSTRACT

An electro-mechanical-type handpiece is specially designed to be used with a laser Generator, particularly those that use a $CO_2$ laser and provide a laser beam in fractional mode. The fractional mode laser beam is provided in a pattern of homogeneous points aligned in rows, columns or diagonally, and such a pattern allows internal tissue along an entire length of a vagina of a patient to be treated and a pelvic floor of the patient to be retracted, such that a urinary bladder of the patient is elevated and, owing to the change in angle thereof, slight or moderate losses of urine are resolved or improved. In addition, the device can be used to treat the inner surface of the vagina of the patient, reducing vaginal laxity caused by childbirth and age.

9 Claims, 3 Drawing Sheets

(51) Int. Cl.
*A61N 1/05* (2006.01)
*A61B 18/00* (2006.01)
(52) U.S. Cl.
CPC .. *A61N 5/0613* (2013.01); *A61B 2018/00196* (2013.01); *A61B 2018/00202* (2013.01); *A61B 2018/00523* (2013.01); *A61B 2018/00559* (2013.01); *A61B 2018/202* (2013.01); *A61B 2018/20553* (2017.05); *A61N 2005/0611* (2013.01); *A61N 2005/0633* (2013.01); *A61N 2005/0644* (2013.01); *A61N 2005/0665* (2013.01)

(56) References Cited

FOREIGN PATENT DOCUMENTS

| ES | 2529390 A1 | 2/2015 |
|----|------------|--------|
| KR | 101363550 B1 | 2/2014 |
| WO | 2015014811 A1 | 2/2015 |
| WO | 2015059120 A1 | 4/2015 |

OTHER PUBLICATIONS

Prados, J. Cuadrado; Written Opinion of the International Searching Authority for International Application No. PCT/ES2016/070856, dated Feb. 16, 2017.
Prados, J. Cuadrado; International Search Report for PCT Application No. PCT/ES2016/070856; dated Feb. 16, 2017.

* cited by examiner

HANDPIECE FOR LASER DEVICE

CROSS REFERENCE TO RELATED APPLICATIONS

This is a Continuation application of International Application Ser. No. PCT/ES2016/070856, filed on Dec. 1, 2016, which claims the benefit of Spanish Application No. 201531355, filed on Dec. 3, 2015, the disclosures of which are hereby incorporated by reference.

BACKGROUND

Aspects of the present invention relate to an electro-mechanical-type handpiece, specially designed to be used with a laser generator to stimulate the regeneration of tissue.

The treatment of bladder leakage (also called urinary incontinence) is a problem associated with the human species, more specifically women. Further, through relevant diagnosis, bladder leakage can be remedied by various types of treatment, some remedies being surgical (e.g., insertion of a mesh) and others non-invasive (e.g., rehabilitation).

What is known as urinary incontinence is a colloquial and generic term, which includes various types and degrees of bladder leakage. Some specialists have classified urinary incontinence as stress incontinence, because urinary incontinence may occur when laughing, coughing, sneezing or when performing any kind of physical effort. On the other hand, imperious incontinence is when the woman feels an immediate and intense need to urinate, and experiences urine leakage before even reaching a bathroom. Further, mixed incontinence is a combination of the preceding two types of incontinence. Moreover, overflow incontinence is when there is a constant accidental leakage of small amounts of urine.

There are numerous causes of urinary incontinence in women, some are short-term and therefore easier to solve and others are long-term as a result of the bladder having no support on the pelvic floor. Short-term causes are the result of urinary tract infections, which result in loss of bladder control, cystitis, and are usually treated with antibiotics.

Other causes of short-term urinary incontinence are polyps, bladder stones, and more sporadically bladder cancer, which generates abnormal tissue masses and induce imperious incontinence being associated with blood in the urine.

In addition to the aforementioned short-term causes, there are long-term causes, such as problems caused by the lack of pelvic support. The so-called pelvic organs hold tissues and muscles in place and, as a result of pregnancy these support systems are weakened or stretched, and therefore the organs being supported are displaced. If the tissues that support the urethra, bladder, uterus, or rectum become weakened, then these organs descend, and bladder leakage may occur.

There are several methods for the treatment of urinary incontinence, from changing one's lifestyle, bladder-sphincter conditioning treatment, physiotherapy, or the use of devices placed in the bladder, medication, injections of mass-forming agents, and ultimately the surgery.

DETAILED DESCRIPTION

Figure 1:
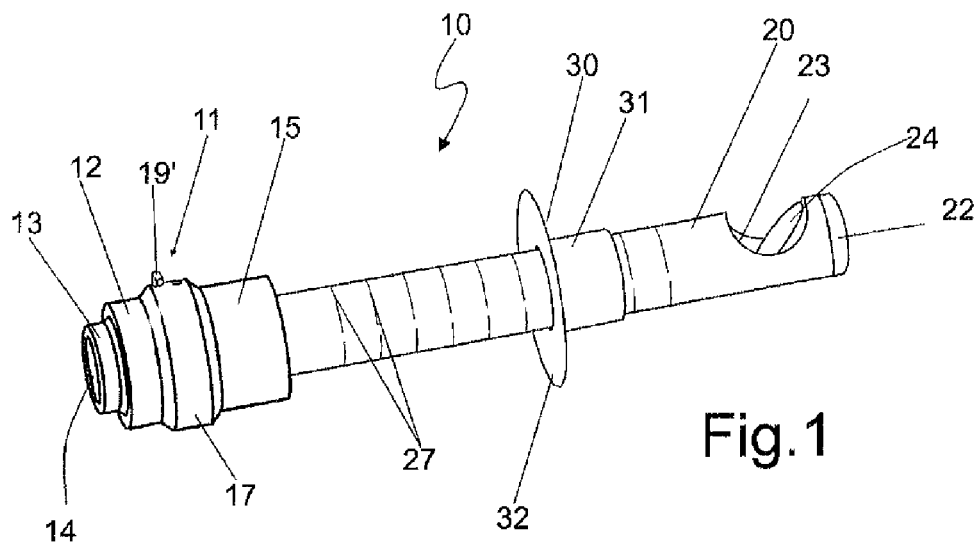
FIG. 1 is a perspective view of the handpiece of the invention, showing parts comprised thereby, such as a revolving mechanism, a cylindrical part and a guide element, according to aspects of the present disclosure.

The purpose of the invention is to provide a handpiece suitable to be used with a laser equipment to stimulate the regeneration of the pelvic tissue with the help of laser beams generated in the relevant device and taken to the specified area inside the vagina to produce small burns, which follow a certain pattern and stimulate the tissue adjacent to these burn dots causing the tissue adjacent to the burn dots to stretch and regenerate restoring the pelvic floor.

In this regard, aspects of the present invention relate to an electro-mechanical-type handpiece, specially designed to be used with a laser generator, particularly those that use a $CO_2$ laser and provide a laser beam in fractional mode. The fractional mode laser beam is provided in a pattern of homogeneous points aligned in rows, columns or diagonally, and such a pattern allows internal tissue along an entire length of a vagina of a patient to be treated and a pelvic floor of the patient to be retracted, such that a urinary bladder of the patient is elevated and, owing to the change in angle thereof, slight or moderate losses of urine are resolved or improved.

In addition, the device can be used to treat the inner surface of the vagina of the patient, reducing vaginal laxity caused by childbirth and age.

The handpiece disclosed in this invention is suitable for use in laser equipment using a $CO_2$ laser and includes means for supplying a laser beam in fractional mode to provide energy impacts on the surface of a tissue according to a pattern of homogeneous points aligned in rows, in columns, or diagonally.

In essence, the handpiece comprises a revolving mechanism and a cylindrical part. The revolving mechanism has an essentially cylindrical configuration, which defines a proximal portion presenting a circular crown delimiting an entrance to which a barrel of a laser generator is coupled. Further, the revolving mechanism includes a distal portion, having a same diameter as the proximal portion, along whose lateral side an open proximal end of the cylindrical part that is hollow inside couples to the distal portion of the revolving mechanism. Moreover, an inner cylindrical surface of the revolving mechanism is in direct contact with the outer cylindrical surface of the proximal end of the cylindrical part when the cylindrical part is coupled to the revolving mechanism.

The revolving mechanism also defines an intermediate portion having a larger outer diameter. The intermediate portion includes a first through hole for positioning a stud and a ventilation through hole (i.e., a second through hole) adapted to blow air into the device.

The cylindrical part is closed at a distal end, which is furthest from the revolving mechanism, and also has an opening on the cylindrical surface near said distal end. The cylindrical part comprises a reflector mirror with an angle of approximately 45° with respect to a longitudinal axis "X", where the mirror is located in an inner portion of the cylindrical part that coincides with the opening of the cylindrical surface. The mirror is internally secured to an inner side of the distal end of the cylindrical part via a support means.

The handpiece also includes an annular-shaped guide element that is displaceably attached to the cylindrical part, in a portion of the outer cylindrical surface that is not coupled to the revolving mechanism.

On the other hand, a proximal end of the cylindrical part has a set of non-through slots on an outer surface, which act as stud positioners. The non-through slots are positioned approximately 30° apart from each other. Further, the cylindrical part is adapted to rotate angularly to the right or left when the position of the stud changes in the set of slots.

In addition, the cylindrical part also includes a set of radially aligned through holes that are parallel to the set of slots, where the set of radially aligned through holes is at the proximal end of the cylindrical part. The set of radially aligned through holes are adapted such that when the hollow cylindrical part rotates angularly to each new position determined by the stud and a slot of the best of slots, the radially aligned through holes come to face the ventilation through hole provided in the revolving mechanism.

The cylindrical part includes marks aligned at a distance that coincides with a length of the pattern created by an impact of the laser beam on the surface of tissue. The marks are along a length and on an outside surface of the cylindrical part not coupled to the revolving mechanism.

On the other hand, the annular-shaped guide element has a configuration with a circular crown from which a rim emerges perpendicularly. The guide element is adapted to position itself at the entrance of the vaginal canal and to allow the longitudinal and angular displacement of the cylindrical part through an interior of the guide element.

In the present invention, the cylindrical part, the inner reflector mirror angled 45° with respect to the longitudinal axis, and the opening of the lateral surface, are positioned such that they allow laser beam pulses coming out of the barrel coupled to the entrance in an axial direction, to be deflected 90° in a radial direction, such that the pulses fall upon the tissue surface of the vaginal canal.

To carry out a desired treatment (e.g., for vaginal relaxation syndrome, urinary incontinence or vaginal rejuvenation) an operator positions the handpiece in the vaginal by inserting the cylindrical part (as if the cylindrical part were a speculum) into said canal and positioning the guide element at the entrance thereof. Subsequently, the opening through which the laser beam pulses will come out is positioned at an initial treatment site; to do this, the cylindrical part slides through the interior of the guide element to a pre-set distance.

Once the opening is positioned at the initial treatment site, controlled laser beam pulses specially designed for each treatment or indication are then emitted producing impacts of laser energy on mucosa and the tissue of the vagina.

The energy impacts are carried out according to previously defined patterns that will delimit an area of impact points perfectly ordered in rows, columns, diagonally, or combinations thereof, with certain lengths.

If treatment so requires, the impacts can be supplied according to a radial or longitudinal distribution within the vaginal canal.

To implement the radial distribution of impacts, the cylindrical part is rotated inside the guide element, and the stud is positioned in a different slot.

The longitudinal distribution of the impacts is carried out by moving the cylindrical part forwards or backwards through the inside of the guide element. The operator is aided by the marks aligned longitudinally on the surface of the cylindrical part, which are distanced at a length matching the length of the energy impact pattern projected on the pelvic floor.

Thus, the laser energy is delivered in fractional mode, applying the patterns on the vaginal tissue in an even and organized way, avoiding superimpositions between impacts and the accumulation of heat in a single area, and also avoiding blank spaces in the vaginal tissue between impacts.

Other details and characteristics will become evident throughout the description that follows, in which reference is made to the drawings attached to this specification, which for the purpose of illustration without limiting the scope of this invention show a graphic representation thereof.

Referring now to the figures, and in particular as noted in FIG. 1, the handpiece 10 of this invention comprises a revolving mechanism 11 with an essentially cylindrical configuration, which defines a proximal portion 12 presenting a circular crown 13 delimiting an entrance 14 to which the head 50 of a laser generator is coupled (see FIG. 6) and a distal portion 15, having the same diameter as the proximal portion 12, along whose lateral side the open proximal end of a cylindrical part 20, that is hollow inside, is coupled. The inner cylindrical surface of the revolving mechanism 11 is in direct contact with the outer cylindrical surface of the end of the coupled cylindrical part 20.

Figure 3:
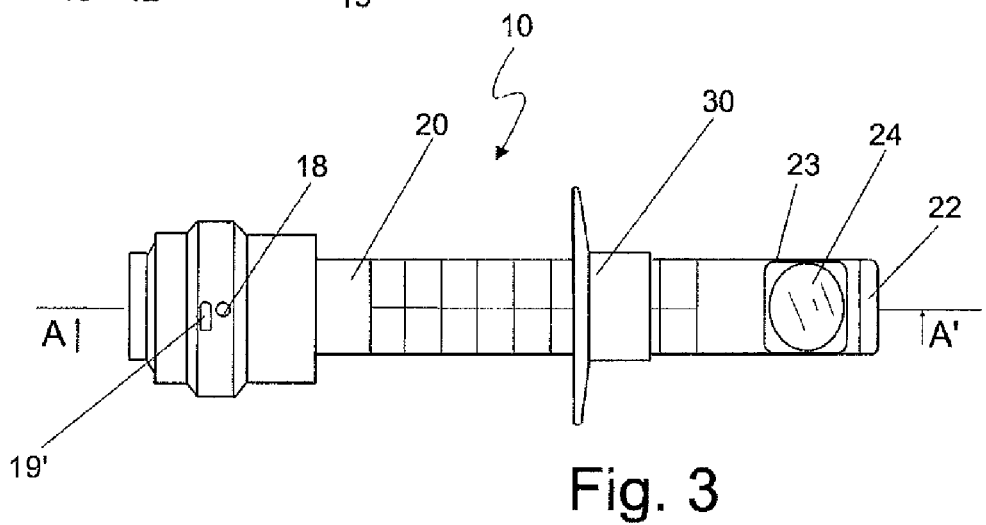
FIG. 3 is a top view of the handpiece of the invention, wherein a hole for positioning a bolt is shown, according to aspects of the present disclosure.
Figure 4:
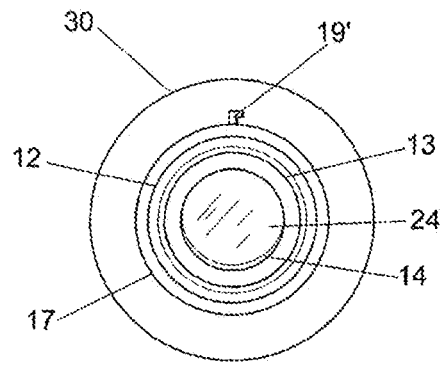
FIG. 4 is a rear view of the handpiece, according to aspects of the present disclosure.

The revolving mechanism 11 also includes an intermediate portion 17 with a larger outer diameter, which, as shown in FIG. 3, is provided with a first through hole 18 for the positioning a stud not shown and a second through hole 19 with a ventilation inlet 19'.

Figure 2:
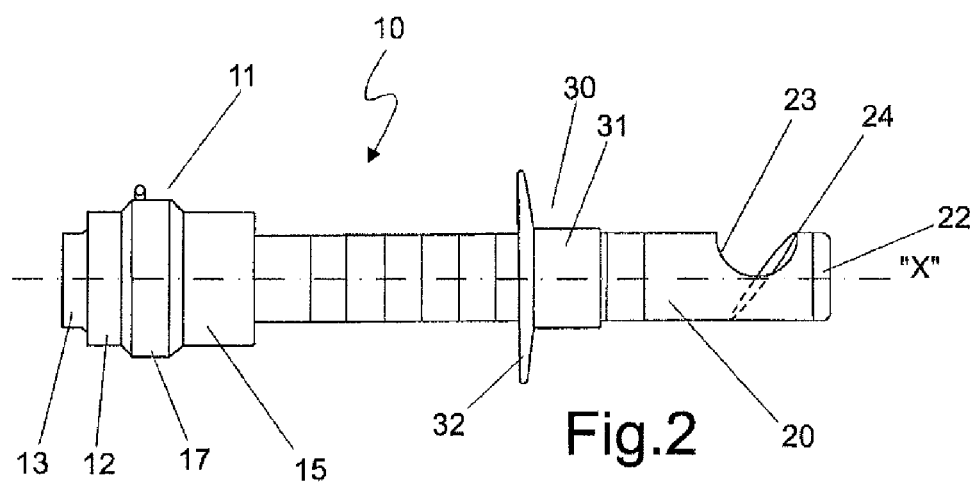
FIG. 2 is a front view of the handpiece, which illustrates an opening, according to aspects of the present disclosure.

According to FIGS. 1, 2 and 3, the cylindrical part 20 is closed at its distal end 22, also includes an opening 23 in a portion of its cylindrical surface near that end, and comprises in a reflector mirror 24 with an angle of approximately 45° with respect to a longitudinal axis "X", this mirror being located, as shown in FIG. 3, in an inner portion coinciding with the opening 24, and internally secured to the side of the distal end 22 of the cylindrical part 20 via a support means.

As illustrated in FIGS. 1 to 7, the handpiece 10 also comprises an annular-shaped guide element 30, which is displaceably attached to the portion of the outer surface of the cylindrical part 20, which is not coupled to the revolving mechanism 11.

In turn, the proximal end of the cylindrical part 20 that is coupled to the revolving mechanism 11, has a set of non-through slots 25 on its outer surface, which act as positioners of the stud which is arranged in the hole 18, said slots having a radial distribution of approximately 30°. The cylindrical part is adapted to rotate angularly to the right or left when the position of the stud changes in the set of slots 25.

Figure 5:
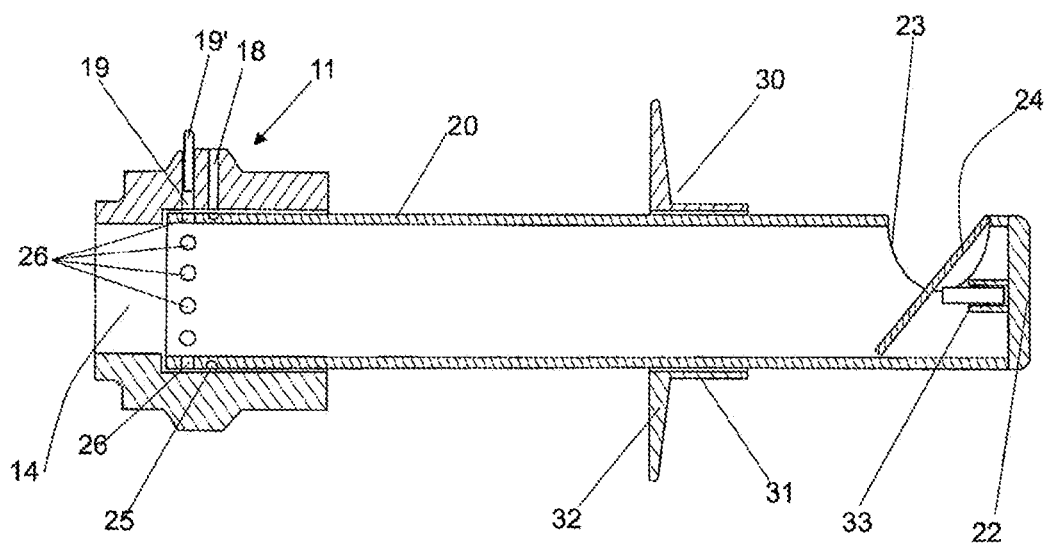
FIG. 5 is a sectioned view according to A-A' in FIG. 3, according to aspects of the present disclosure.

In addition, as illustrated in FIG. 5, the proximal end of the cylindrical part 20 includes on its cylindrical surface, a set of through holes 26, radially aligned and parallel to the set of slots 25. The set of holes 26 is arranged such that, when the cylindrical part 20 rotates angularly to each position determined by the combination of the stud (not shown) and a slot 25, one of said holes 26 always comes to face the ventilation through hole 19 provided in the revolving mechanism 11. This arrangement allows air to be blown into the handpiece regardless of the angular position adopted, and thus prevents the fumes emitted by vaporization from fogging the laser targeting lens.

According to what is illustrated in FIGS. 1 to 3, the cylindrical part 20 includes on its outside surface and along the whole length of its portion not coupled to the revolving mechanism 11, marks 27 aligned at a distance that coincides with the length of the pattern created by the impact of the laser beam on the surface of the tissue. This characteristic allows that, during the treatment, once a first impact has been made with the laser beam on the tissue, the cylindrical part 20 can slide through the inside of the guide element 30 removing a measurement, and this ensures that the new impact of the laser beam on the tissue is carried out on a consecutive area, without leaving spaces between impact areas, and without the impacts overlapping.

Figure 6:
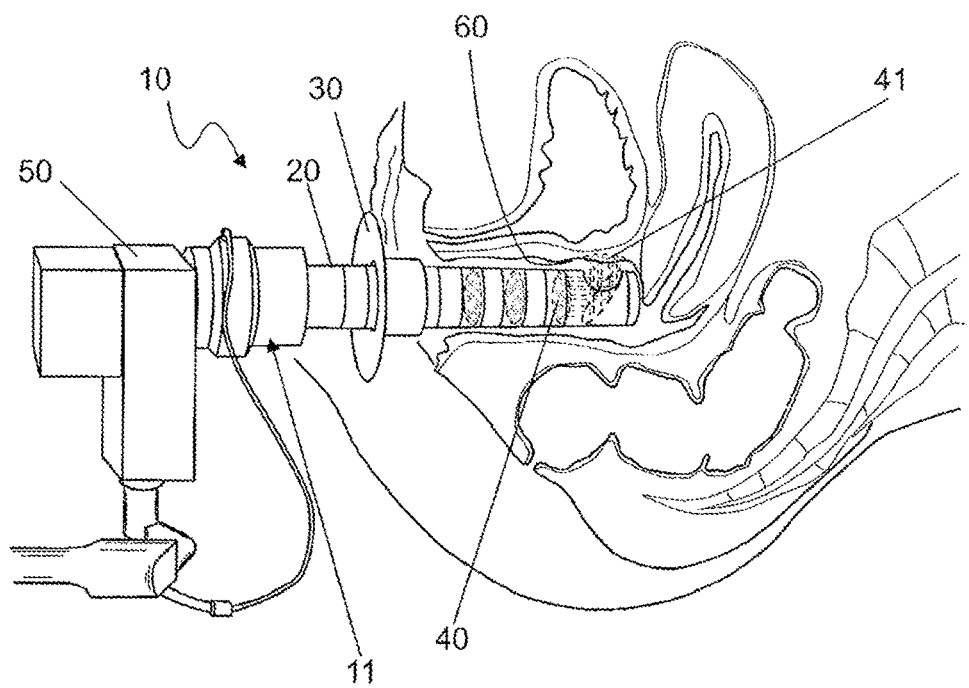
FIG. 6 is an illustration of the handpiece coupled to a head and inserted into a vaginal cavity, according to aspects of the present disclosure.

FIGS. 1 to 3 depict the guide element 30, which is annular-shaped and presents a circular crown configuration 31 from which a rim 32 emerges perpendicularly, such guide element 30 being adapted to position itself at the entrance of the vaginal canal 60, as shown in FIG. 6, and allow the longitudinal and angular displacement of the cylindrical part 20 inside the canal.

FIG. 6 graphically illustrates the positioning of the handpiece inside the vagina at the time of treatment. This figure shows that the laser beam pulses 40 from the head 50 located at the entrance 14 are directed towards the mirror 24, which has a 45° rotation angle, directing them through the opening 23 towards the pelvic floor, causing thermal impact 41. The longitudinal distribution of impacts 41 is carried out by moving the cylindrical part 20 forwards or backwards along the inside of the guide element 30, with the help of the marks 27. The angular distribution of impacts 41 is carried out by rotating the cylindrical part 20 along the inside of the guide element 30 and securing the stud in another slot 25.

Figure 7:
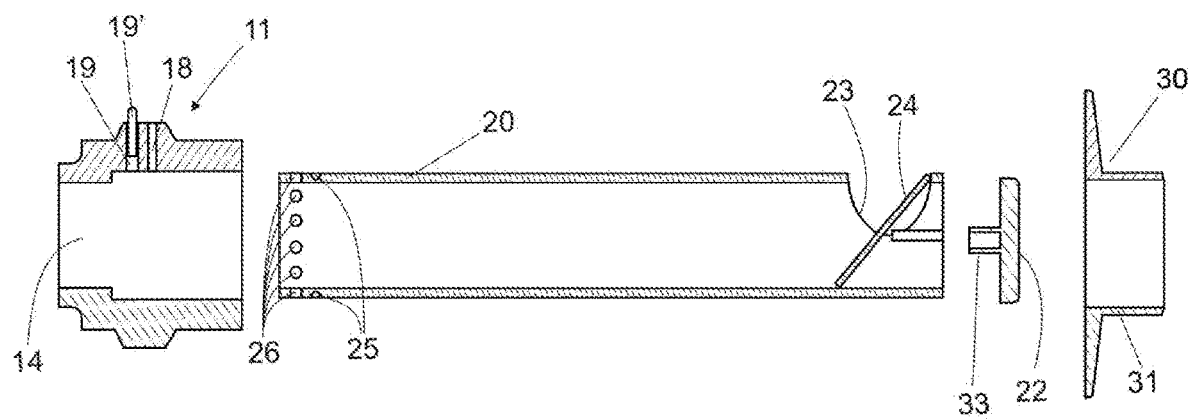
FIG. 7 is an exploded view of the sectioned view of FIG. 5, according to aspects of the present disclosure.

FIG. 7 illustrates an embodiment of the handpiece of FIG. 5 separated into three basic components: the revolving mechanism 11, the cylindrical part 20, and the guide element 30. As recited above, the revolving mechanism 11 includes an entrance 14 to which a head of a laser generator may be coupled. Further, the revolving mechanism 11 includes a first hole 18 for positioning a stud (not shown) within the handpiece. Specifically, when the first hole 18 lines up with a hole from a set of slots 25 of the cylindrical part 20, the stud will be in both the hole 18 and a slot 25, so the operator knows that the handpiece is in a configuration to allow impacts from the laser at a proper position.

Moreover, the revolving mechanism 11 includes a second hole 19 (i.e., a ventilation hole) with a ventilation inlet 19', as discussed above. When the stud is lined up in one of the slots 25, a ventilation hole 26 on the cylindrical part 20 lines up with the ventilation hole 19 of the revolving mechanism 11. Thus, air may be blown into the handpiece regardless of the angular position of the handpiece, as discussed above. The cylindrical mechanism 20 further includes an opening 23 and a mirror 24, as discussed above. A distal end 22 with a channel 33 couples to the cylindrical part 20. As discussed above, the annular guide element 30 includes a crown 31, where an aperture of the annular guide element 30 receives the cylindrical part 20 and acts as a guide for positioning the handpiece in the vaginal canal.

Having sufficiently described the present invention in correspondence with the annexed figures, it is easy to understand that they may be subject to any modifications in detail as deemed suitable as long as the essence of the invention is not altered, this being summarized in the following claims.

What is claimed is:

1. A handpiece for a laser device for supplying a laser beam in fractional mode and which is adapted to provide energy impacts on a specified area inside a vagina, the energy impacts comprising small burns which follow a certain pattern of homogeneous burn points aligned in rows, columns, or diagonally so that the pattern of burn points stimulates tissue adjacent to these burn dots which causes the tissue to stretch, the handpiece being configured to be coupled to a barrel of a laser generator, wherein the handpiece comprises:

a revolving mechanism with an essentially cylindrical configuration, which defines a proximal portion presenting a circular crown delimiting an entrance to which the barrel of a laser generator may be coupled, and a distal portion, having the same diameter as the proximal portion, wherein an open proximal end of a cylindrical part is coupled to an inner lateral side of the revolving mechanism;

the cylindrical part being hollow inside, wherein the inner lateral side of the revolving mechanism is in direct contact with an outer lateral surface of the proximal end of the cylindrical part, the cylindrical part being closed at a distal end and comprises:

an opening in a portion of a surface near the distal end, and a one-face reflector mirror inside the cylindrical part, wherein the mirror is angled approximately 45° with respect to a longitudinal axis, the mirror being located in an interior portion of the cylindrical part coinciding with the opening, and being secured to the interior of the distal end of the cylindrical part by a support means; and an annular-shaped guide element, which is displaceably attached to a portion of the cylindrical part that is not directly coupled to the revolving mechanism.

2. The handpiece according to claim 1, wherein the revolving mechanism also defines an intermediate portion with a greater diameter, in which a first through hole is provided, for the positioning of a stud, and a second ventilation through hole, adapted to blow air into the handpiece.

3. The handpiece according to claim 1, wherein the proximal end of the cylindrical part has a set of slots on a surface of the cylindrical part, wherein slots act as stud positioners, presenting a radial distribution of approximately 30° between each slot, so that the cylindrical part being adapted to turn angularly to the right or left when the position of the stud changes in the set of slots.

4. The handpiece according to claim 1, wherein the proximal end of the hollow cylindrical part has a set of radially aligned through holes on its lateral surface, wherein the radially aligned through holes are adapted such that when the cylindrical part rotates angularly to each position determined by the combination of the stud and a slot, one of said holes comes to face the ventilation hole provided in the revolving mechanism.

5. The handpiece according to claim 1, wherein the cylindrical part presents on its outer surface annular marks aligned longitudinally at a distance that coincides with the amplitude of the pattern of homogeneous points created by the impact of the laser beam on the tissue surface.

6. The handpiece according to claim 1, wherein the annular-shaped guide element has a configuration with a circular crown from which a rim emerges perpendicularly, the guide element being adapted to position itself at the entrance of the vaginal canal and to allow the axial and angular displacement of the cylindrical part through its interior.

7. The handpiece according to claim 1, wherein the reflector mirror and the opening are positioned such that the mirror allows the laser beam pulses coming out of the barrel in an axial direction, to be deflected 90° in a radial direction, to fall upon the tissue surface of the vaginal canal.

8. The handpiece according to claim 1, wherein the handpiece is adapted for being coupled to a $CO_2$ type laser generator.

9. The handpiece according to claim 1, wherein the one face reflector mirror is a flat mirror.

* * * * *